(12) United States Patent
Okada et al.

(10) Patent No.: US 8,382,729 B2
(45) Date of Patent: Feb. 26, 2013

(54) ADHESIVE PATCH

(75) Inventors: Tomomi Okada, Tokyo (JP); Shigeo Ohta, Tokyo (JP); Nobuo Tsutsumi, Tokyo (JP)

(73) Assignee: Hisamitsu Pharmaceutical Co., Inc., Tosu-Shi, Saga (JP)

( * ) Notice: Subject to any disclaimer, the term of this patent is extended or adjusted under 35 U.S.C. 154(b) by 239 days.

(21) Appl. No.: 12/864,183

(22) PCT Filed: Jan. 22, 2009

(86) PCT No.: PCT/JP2009/050987
§ 371 (c)(1),
(2), (4) Date: Aug. 24, 2010

(87) PCT Pub. No.: WO2009/096315
PCT Pub. Date: Aug. 6, 2009

(65) Prior Publication Data
US 2010/0318042 A1    Dec. 16, 2010

(30) Foreign Application Priority Data
Jan. 31, 2008  (JP) ................ P2008-021636

(51) Int. Cl.
*A61F 13/02*  (2006.01)
(52) U.S. Cl. ...................... 604/307; 424/443
(58) Field of Classification Search .............. 604/307; 424/443
See application file for complete search history.

(56) References Cited

U.S. PATENT DOCUMENTS

| | | | |
|---|---|---|---|
| 5,478,567 A | 12/1995 | Nakagawa et al. | |
| 5,607,388 A * | 3/1997 | Ewall | 602/58 |
| 6,914,169 B1 | 7/2005 | Oota et al. | |
| 6,924,410 B2 | 8/2005 | Tsuruda et al. | |

(Continued)

FOREIGN PATENT DOCUMENTS

| | | |
|---|---|---|
| CN | 1409628 A | 4/2003 |
| EP | 1 072 261 A2 | 1/2001 |

(Continued)

OTHER PUBLICATIONS

English translation of the International Preliminary Report on Patentability (Chapter 1 of the Patent Cooperation Treaty) issued on Aug. 3, 2010, in International Application No. PCT/JP2009/050987.

(Continued)

*Primary Examiner* — Tatyana Zalukaeva
*Assistant Examiner* — Benjamin Klein
(74) *Attorney, Agent, or Firm* — Nath, Goldberg & Meyer; Joshua B. Goldberg; Sheldon M. McGee

(57) ABSTRACT

Provided is an adhesive patch including a stretchable support and an adhesive layer laminated on at least one side of the support, wherein the stretchable support comprises a woven fabric knitted in stockinette stitch on both sides having two or more rows of crimped polyethylene terephthalate multifilament yarns, the adhesive layer contains 25 to 50% by mass of a liquid organic ingredient and 25 to 50% by mass of a thermoplastic elastomer based on the total mass of the layer and contains 10% by mass or more of methyl salicylate as the liquid organic ingredient based on the total mass of the layer, and the storage elastic modulus (G') of the adhesive layer is 30000 to 75000 Pa at 10 rad/s and 37° C.

6 Claims, 6 Drawing Sheets

U.S. PATENT DOCUMENTS

| | | |
|---|---|---|
| 7,250,546 B2 | 7/2007 | Tsuruda et al. |
| 2002/0031542 A1 | 3/2002 | Takada et al. |
| 2003/0138479 A1* | 7/2003 | Mizota et al. ............... 424/443 |
| 2006/0198880 A1 | 9/2006 | Hashimoto et al. |
| 2006/0263420 A1 | 11/2006 | Hirano et al. |
| 2010/0168634 A1* | 7/2010 | Leeming et al. ............... 602/44 |

FOREIGN PATENT DOCUMENTS

| | | |
|---|---|---|
| JP | 10-109945 A | 4/1998 |
| JP | 2816765 B2 | 8/1998 |
| JP | 2001-39864 A | 2/2001 |
| JP | 2001-508053 A | 6/2001 |
| JP | 2001-328935 A | 11/2001 |
| JP | 2003-169823 A | 6/2003 |
| JP | 3499247 B2 | 12/2003 |
| JP | 2004-121828 A | 1/2004 |
| JP | 2005-187331 A | 7/2005 |
| JP | 2006-045101 A | 2/2006 |
| JP | 2006-248996 A | 9/2006 |
| JP | 2007-15963 A | 1/2007 |
| JP | 2007-015963 A | 1/2007 |
| JP | 2007-151916 A | 6/2007 |
| JP | 4705301 B2 | 3/2011 |
| JP | 4664281 B2 | 4/2011 |
| JP | 4927403 B2 | 2/2012 |
| RU | 2194496 C2 | 12/2002 |
| WO | 01/43729 A1 | 6/2001 |
| WO | 01/68061 A1 | 9/2001 |
| WO | 2005/092265 A1 | 10/2005 |
| WO | 2006/095820 A1 | 9/2006 |
| WO | 2006/129745 A1 | 12/2006 |

OTHER PUBLICATIONS

Office Action issued on Jul. 6, 2011 in a counterpart Chinese patent application (No. 200980103647.4), six pages total with English translation of relevant parts.

Toyama, Mitsuo, "Pressure Sensitive Adhesives (Adhesive Compounds)—Its Function and Mechanism-", 1992, pp. 14-18, 1st Edition, 2nd Print, Mamoru Nishiguchi, Kyoto, Japan.

Martin, Debra et al., "Dermal Absorption of Camphor, Menthol, and Methyl Salicylate in Humans", Journal of Clinical Pharmacology, 2004, pp. 1151-1157, vol. 44, SAGE.

Celanese Acetate Complete Textile Glossary, 2001, p. 40.

Notice of Allowance for RU Patent Application No. 2010136318, issued on Aug. 3, 2012.

* cited by examiner

ADHESIVE PATCH

TECHNICAL FIELD

The present invention relates to an adhesive patch containing methyl salicylate.

BACKGROUND ART

Conventionally, as anti-inflammatory analgesics for external use, irrespective of patches substantially free from moisture in an adhesive or cataplasms containing moisture in an adhesive, those containing a nonsteroidal anti-inflammatory agent such as a salicylic acid-based compound, indomethacin, diclofenac or ketoprophen and 1-menthol as a cooling agent as the active ingredient have been frequently used.

In general, while cataplasms having an anti-inflammatory analgesic action for external use cause less skin irritation and are excellent in cooling effect in order to further enhance the effect, there has been a problem of coming off due to poor adhesion to the skin. On the other hand, while patches substantially free from moisture are excellent in adhesion to the skin, it may be accompanied by pain in some cases when peeling off. Incidentally, as the adhesive patch suppressing such pain, those described in Patent Document 1 are suggested.

Patent Document 1: National Publication of International Patent Application No. 2001-508053

DISCLOSURE OF THE INVENTION

In patches containing a salicylic acid-based compound, methyl salicylate as medicinal properties needs to be highly formulated since a plaster is thin as compared to aqueous cataplasms, and in this case, since methyl salicylate itself acts as a plasticizer, come-off (drop-off) may occurs when applied, or flexibility of an adhesive layer may vary due to the volatilization of methyl salicylate, and thus a problem thereof is that continuous application properties become difficult to control.

Specifically, the adhesive patch containing methyl salicylate is applied to the joints of the limbs in many cases, and the adhesive patch has a tendency to come off by an effect from the joints frequently having a twisting motion besides an expanding and contracting motion.

Since the adhesive patch is used by applying to the skin or the like, appropriate application properties are obviously desired, and the continuity of stimulation generated by exerting anti-inflammatory analgesic effects is particularly important. However, it was not easy to achieve the adhesive patch simultaneously comprising excellent application properties and the continuity of stimulation by applying the conventionally known method including the above-described publication.

Therefore, the present invention has been made in consideration of the situations described above, and an object is to provide an adhesive patch excellent in application properties and the continuity of stimulation.

The present inventors have conducted intensive studies in order to solve the problems described above and consequently found that an adhesive patch comprising an adhesive layer containing 25 to 50% by mass of a liquid ingredient (10% by mass or more is methyl salicylate) and 25 to 50% by mass of a thermoplastic elastomer, which is formed on a support having particular stretchability, and one with the adhesive layer having a particular storage elastic modulus is an adhesive patch which has good continuous application properties and does not come off even upon twisting motion of the joints and is excellent in the continuity of stimulation, whereby the present invention has been accomplished.

More specifically, the present invention provides an adhesive patch comprising a stretchable support and an adhesive layer laminated on at least one side of the support, in which the stretchable support comprises a woven fabric knitted in stockinette stitch on both sides having two or more rows of crimped polyethylene terephthalate multifilament yarns, the adhesive layer contains 25 to 50% by mass of a liquid organic ingredient and 25 to 50% by mass of a thermoplastic elastomer based on the total mass of the layer and contains 10% by mass or more of methyl salicylate as the liquid organic ingredient based on the total mass of the layer, and the storage elastic modulus (G') of the adhesive layer is 30000 to 75000 Pa at 10 rad/s and 37° C.

The adhesive patch of the present invention uses the particular support described above, and the adhesive layer contains 25 to 50% by mass of a liquid organic ingredient based on the total mass of the layer, 10% by mass or more of methyl salicylate of the liquid organic ingredient based on the total mass of the layer and 25 to 50% by mass of a thermoplastic elastomer based on the total mass of the layer, whereby good application properties can be maintained. In addition, when the content of thermoplastic elastomer is within this range, good cohesion and shape retention of the adhesive layer can be maintained, whereby good application properties can be obtained. Furthermore, the storage elastic modulus (G') of the adhesive layer is 30000 to 75000 Pa at 10 rad/s and 37° C., whereby drug release properties and percutaneous absorbability improve, and the continuity of stimulation improves. The stretchable support is a woven fabric knitted in stockinette stitch on both sides having two or more rows of crimped polyethylene terephthalate multifilament yarns, thereby having sufficient stretchability, and thus when the adhesive patch of the present invention is topically applied to, for example, the limbs such as the elbows and knees, coming off and dropping off occur less often.

In addition, it is preferred that the thermoplastic elastomer is at least one selected from the group consisting of a styrene-isoprene-styrene block copolymer, a styrene-butadiene-styrene block copolymer, a styrene-isoprene rubber, a styrene-butadiene rubber, polyisoprene, polybutadiene, polyisobutylene and a silicone rubber. Since these thermoplastic elastomers are easy to handle and cause relatively less unnecessary irritation to the skin, these are preferably used.

Furthermore, it is preferred that the adhesive layer contains a rosin-based resin and/or petroleum-based resin as a tackifier. In this case, appropriate tackiness and flexibility can be imparted to the adhesive layer.

It is preferred that the content of the tackifier is 10 to 30% by mass based on the total mass of the adhesive layer. In this case, the adhesion of the adhesive layer is maintained in an appropriate range, and the resulting adhesive patch can be prevented from coming off when applied and from causing pain when peeled off.

It is preferred that the woven fabric has a basis weight of 80 to 150 g/m² and has a longitudinal (long axis direction) modulus of 2 to 12 N/5 cm and a lateral (short axis direction) modulus of 2 to 8 N/5 cm. When the basis weight is within this range, upon applying the adhesive to a knitted fabric, an adhesive base does not seep through the stitches of the knitted fabric, and anchor properties between the knitted fabric and the adhesive base can be firmly maintained, and it is possible to further improve application properties as an adhesive patch. When each modulus is within this range, an adhesive patch excellent in drug release properties and application properties can be made.

It is preferred that the moisture vapor permeability of the entire adhesive patch measured at a temperature of 40° C. and a relative humidity of 90% is 1 to 350 g/m²·24 hr. In this case, volatile methyl salicylate and 1-menthol that may be formulated are unlikely to volatile and can be stably held in the adhesive, thereby the topical percutaneous absorption of the effective amount of the drug is possible when the adhesive patch is applied, and also it is possible to minimize the change in the amount of a volatile substance, and thus continuous application properties can be secured.

EFFECT OF THE INVENTION

According to the present invention, the adhesive patch that comprises good application properties, has improved drug release properties and percutaneous absorbability and is excellent in the continuity of stimulation is provided.

BEST MODES FOR CARRYING OUT THE INVENTION

Figure 1:
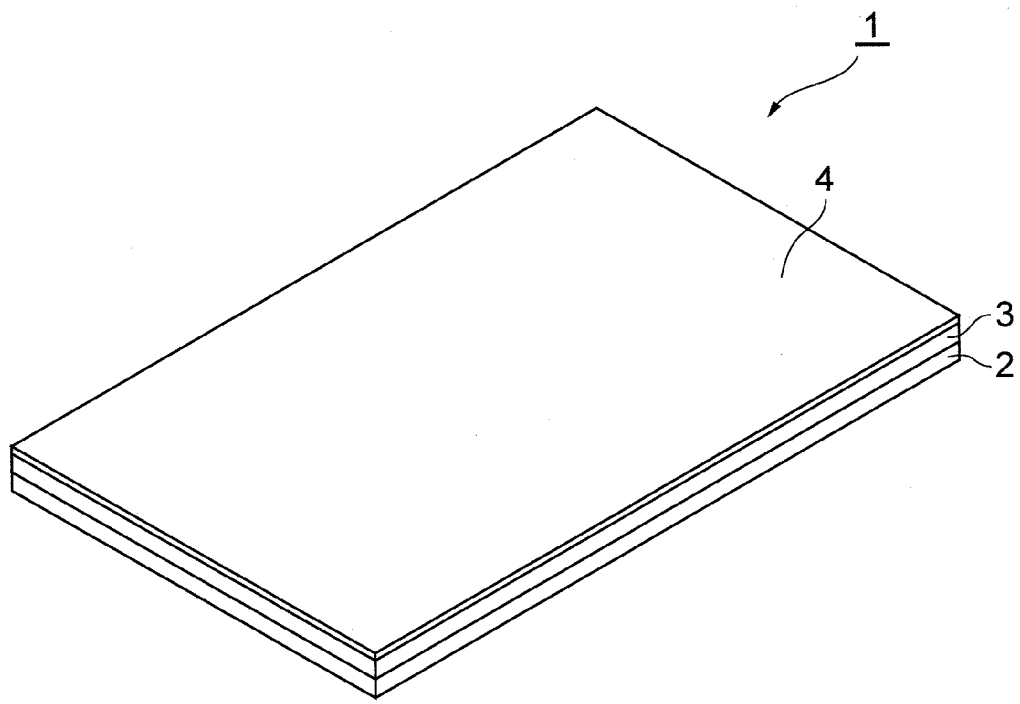
FIG. 1 is a perspective view showing a preferred embodiment of the adhesive patch of the present invention.

Hereinafter, suitable embodiments of the adhesive patch of the present invention will be described referring to the drawings in some cases. Incidentally, in the drawings, the same element is denoted by the same symbol, and the duplicate explanation is omitted. In addition, the positional relation such as top, bottom, left and right is based on the positional relation shown in the drawings unless otherwise noted. Furthermore, the dimension and proportion of the drawings are not limited to the shown proportion.

FIG. 1 is a perspective view showing a preferred embodiment of the adhesive patch of the present invention. In FIG. 1, adhesive patch 1 is comprised by support 2, adhesive layer 3 disposed on the support 2, and release sheet 4 disposed on the adhesive layer 3. The adhesive patch 1 is used after peeling the release sheet 4, by applying such that the adhesive layer 3 is firmly attached on the skin of patient or the like.

First, the stretchable support 2 will be described.

Figure 2:
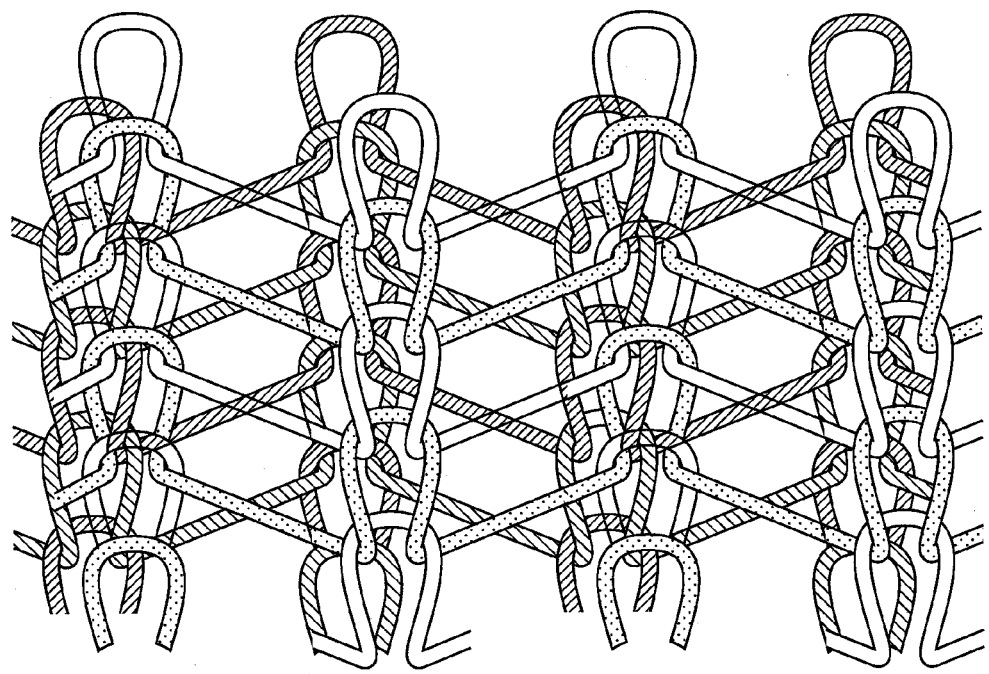
FIG. 2 is a schematic view showing a mesh construction of stockinette stitch on both sides having two rows of multifilament yarns.

The support 2 used in the present invention is a woven fabric (knitted fabric) knitted in stockinette stitch on both sides having two or more rows of crimped polyethylene terephthalate multifilament yarns. In FIG. 2, a schematic view showing a mesh construction of stockinette stitch on both sides having two rows of multifilament yarns is shown. Incidentally, in FIG. 2, hatching is used to define the mesh construction, and it is not intended that the kind of yarns are different.

For the knitted fabric as the support 2, it is preferred that its basis weight (mass per unit) is 80 to 150 g/m². In this range, when the adhesive described later is applied to the knitted fabric, an adhesive base (which refers to an ingredient having adhesion, among the ingredients constituting the adhesive layer 3; the same applies hereinafter) does not seep through the stitches of the knitted fabric, and anchor properties with the adhesive base in the present invention can be firmly maintained, and even doing the motion twisting the joints of the limbs upon application, the adhesion state can be firmly maintained, and an adhesive is not remained upon peeling.

In addition, it is preferred that the support 2 has a longitudinal (long axis direction) modulus of 2 to 12 N/5 cm and a lateral (short axis direction) modulus of 2 to 8 N/5 cm measured according to the method of JIS L1018. Incidentally, the longitudinal direction referred herein refers to the flow direction in the process for producing a woven fabric, and the lateral direction refers to the direction perpendicular to the longitudinal direction, i.e., width direction. When the longitudinal or lateral modulus is lower than 2 N/5 cm, the adhesive tends to seep into the stitches due to the stretched knitted fabric when the adhesive is applied thereto, and functions as the adhesive patch tend to be reduced, in addition, when the longitudinal modulus is higher than 12 N/5 cm or the lateral modulus is higher than 8 N/5 cm, it is poor in stretchability, and partial coming off tends to occur due to twisting of the skin when applied to a bend of the body. Incidentally, the modulus is the value at room temperature (25° C.).

Next, the adhesive layer 3 will be described.

The adhesive layer 3 of the present invention comprises an adhesive, and this adhesive contains methyl salicylate that is a drug and an adhesive base as essential ingredients. The content of the liquid organic ingredient in the adhesive layer 3 is 25 to 50% by mass based on the total mass of the adhesive layer. Incidentally, the liquid organic ingredient is an organic substance that is fluid at room temperature (25° C.). Of them, the content of methyl salicylate is 10% by mass or more based on the total mass of the adhesive layer. The adhesive patch 1 of the present invention with these concentration ranges has the predetermined support 2 described above, whereby good application properties can be maintained. The content of the methyl salicylate is preferably 10 to 15% by mass, more preferably 10 to 12% by mass, based on the total mass of the adhesive layer since sufficient drug release properties and percutaneous absorbability can be maintained.

The adhesive layer 3 contains a thermoplastic elastomer contained in the adhesive base in an amount of 25 to 50% by mass based on the total mass of the adhesive layer 3 besides the active ingredients described above. It is preferred that the content of the thermoplastic elastomer is 30 to 45% by mass. When the content is below 25% by mass, elasticity tends to be weakened, and when the content exceeds 50% by mass, shape retention tends to be poor. Examples of the adhesive base include, besides thermoplastic elastomer-based adhesives, acrylic adhesives, rubber-based adhesives (except for the former two adhesives), polyurethane-based adhesives, silicone-based adhesives, and adhesives comprising a mixture thereof.

Examples of the thermoplastic elastomer-based adhesives include those containing a thermoplastic elastomer and a tackifier, but when the thermoplastic elastomer itself has adhesion, the use of the tackifier is not essential. Examples of the thermoplastic elastomer that can be used in the thermoplastic elastomer-based adhesives include styrene-isoprene-styrene block copolymers, styrene-butadiene-styrene block copolymers, polyvinyl acetate, ethylene-vinyl acetate copolymers, styrene-isoprene rubbers, styrene-butadiene rubbers, polyisoprene, polybutadiene, polyisobutylene, and silicone rubbers, and one or two or more selected from these may be contained. Of them, a thermoplastic elastomer-based adhesive using a styrene-isoprene-styrene block copolymer is preferable from the viewpoint of cohesiveness, weather resistance, aging resistance, and chemical resistance.

Examples of the styrene-isoprene-styrene block copolymers include Cariflex TR-1107, TR-1111, TR-1112, and TR-1117 (all from Shell Chemicals Ltd.), Quintac 3530, 3421, and 3570C (all from Zeon Corp.), JSR SIS-5000 and JSR SIS-5002 (all from Japan Synthetic Rubber Co., Ltd.), Krayton D-KX401CS and D-1107CU (all from Shell Chemicals Ltd.), and Solprene 428 (Phillip Petroleum Company), and one of them or a combination of two or more of them can be used.

Examples of the acrylic adhesives include an adhesive in which at least one of (meth)acrylic monomer such as (meth)acrylic acid, 2-ethylhexyl (meth)acrylate, octyl (meth)acrylate, methyl (meth)acrylate, butyl (meth)acrylate, hydroxyethyl (meth)acrylate, glycidyl (meth)acrylate, and methoxyethyl (meth)acrylate is polymerized or copolymerized at a monomer ratio that exerts adhesion at a use temperature of the adhesive patch. Here, (meth)acryl means acryl or methacryl. The same applies to other usages such as (meth)acrylate. Incidentally, a monomer other than the (meth)acrylic monomers (e.g., vinyl acetate) can be used as a monomer for the copolymerization. Since the acrylic adhesives themselves usually have adhesion, the addition of a tackifier is not essential, however, a tackifier may be added to control tackiness, the elastic modulus or the like.

The acrylic adhesive is preferably a copolymer comprising a high-Tg monomer (monomer having a glass transition temperature higher than room temperature when homopolymerized) and a low-Tg monomer (monomer having a glass transition temperature lower than room temperature when homopolymerized) in combination. (Meth)acrylic acid which is polar and contributes to high adhesiveness is suitable as the high-Tg monomer, and (meth)acrylic acid ester containing an alkyl group having 4 to 12 (preferably, 4 to 8) carbon atoms (a hydrogen atom in the alkyl group may be substituted by a hydroxy group) is suitable as the low-Tg monomer.

Examples of the rubber-based adhesives include natural rubber-based adhesives and polyisobutylene-based adhesives. The natural rubber-based adhesives comprise a natural rubber and a tackifier, and the polyisobutylene-based adhesives comprise polyisobutylene having various molecular weights and various additives may be added thereto, if necessary. It is particularly preferred that the adhesive comprising polyisobutylene is used as a mixture with a styrene-isoprene-styrene block copolymer.

Examples of the polyurethane-based adhesives include aliphatic polyurethane adhesives and aromatic polyurethane adhesives, and examples of the silicone-based adhesives include an adhesive containing a crude rubber of silicone such as a polydimethylsiloxane polymer, polymethylvinylsiloxane or polymethylphenylsiloxane and an MQ resin (silicone resin with a three-dimensional structure comprising an "M unit" such as $(CH_3)_2SiO_{1/2}$ and a "Q unit" such as $SiO_2$).

The content of the adhesive base comprising the thermoplastic elastomer, the tackifier and the like is preferably 35 to 90% by mass, more preferably 40 to 85% by mass, based on the total mass of the adhesive layer, from the viewpoint of the cohesion and shape retention of the adhesive layer 3.

The thermoplastic elastomer-based adhesives and the rubber-based adhesives that are the adhesive base usually contain a tackifier for exerting adhesion. A tackifier can be added even to an adhesive base having adhesion by itself without the addition of the tackifier. Such a tackifier is preferably a rosin-based resin and/or a petroleum-based resin. Examples of the rosin-based resin include natural resin rosin, denatured rosin, rosin ester (such as rosin glycerin ester or rosin pentaerythritol ester), and hydrogenated rosin ester (such as hydrogenated rosin glycerin ester or hydrogenated rosin pentaerythritol ester). among them, hydrogenated rosin ester is preferable from the viewpoint of skin irritation and aging resistance, and hydrogenated rosin glycerin ester is particularly preferable. Specific examples of such a rosin-based resin include Ester Gum H and Pinecrystal KE-100 and KE-311 (all from Arakawa Chemical Industries, Ltd.), Foral 85, Foral 105, Staybelite Ester 7, Staybelite Ester 10 (all from Rika-Hercules, Inc.), and the like, and one of them or a combination of two or more of them can be used.

Moreover, examples of the petroleum-based resin include C5 synthetic petroleum resins (such as copolymers comprising at least two kinds of isoprene, cyclopentadiene, 1,3-pentadiene, and 1-pentene; copolymers comprising at least two kinds of 2-pentene and dicyclopentadiene; and resins mainly composed of 1,3-pentadiene), C9 synthetic petroleum resins (such as copolymers comprising at least two kinds of indene, styrene, methylindene, and α-methylstyrene), dicyclopentadiene-based synthetic petroleum resins (such as copolymers with isoprene and/or 1,3-pentadiene mainly composed of dicyclopentadiene), and the like, and C9 synthetic petroleum resins are preferable from the viewpoint of weather resistance and compatibility with the adhesive base.

Moreover, examples of the petroleum resin include alicyclic petroleum resins (alicyclic hydrocarbon resins such as alicyclic saturated hydrocarbon resins), alicyclic hydrogenated petroleum resins, aliphatic petroleum resins (aliphatic hydrocarbon resins), aliphatic hydrogenated petroleum resins, aromatic petroleum resins and the like, from the viewpoint of another classification, and alicyclic petroleum resins and alicyclic hydrogenated petroleum resins are preferable from the viewpoint of adhesion, compatibility with the adhesive base, and aging resistance, and alicyclic hydrogenated petroleum resins are particularly preferable. Specific examples of such a petroleum-based resin include Arkon-P70, Arkon P-90, Arkon P-100, Arkon P-115, and Arkon P-125 (all from Arakawa Chemical Industries, Ltd.), Escoretz 8000 (Esso Chemical Ltd.), and the like, and one of them or a combination of two or more of them can be used.

Incidentally, the adhesive layer 3 may further contain, in addition to the rosin-based resin and/or the petroleum-based resin described above, other kinds of tackifiers such as terpene-based resins, phenol-based resins, and xylene-based resins.

The above-described tackifier is contained in an amount of 10 to 30% by mass and preferably 15 to 25% by mass based on the total mass of the adhesive layer of the adhesive patch 1 of the present invention. Incidentally, when the content described above is less than 10% by mass, physical properties of adhesion are likely to decline, and coming off is likely to occur when applied, when the content exceeds 30% by mass, it might accompany the incidence of irritation and pain when peeled off.

The adhesive layer 3 in the adhesive patch 1 of the present invention may contain an absorption promoter, in addition to the drug, the adhesive base and the tackifier described above. Such an absorption promoter may be a compound whose effect of promoting absorption into the skin has been conventionally recognized, and examples thereof include: (1) fatty acid, aliphatic alcohol, fatty acid amide, and fatty acid ether having 6 to 20 carbon chains (they may be saturated or unsaturated and may be cyclic, linear, or branched); (2) aromatic organic acid, aromatic alcohol, aromatic organic acid ester, and ether; and (3) lactic acid esters, acetic acid esters, monoterpene-based compounds, sesquiterpene-based compounds, Azone, Azone derivatives, glycerin fatty acid esters, propylene glycol fatty acid esters, sorbitan fatty acid esters (Span type), polysorbates (Tween type), polyethylene glycol fatty acid esters, polyoxyethylene hydrogenated castor oils (HCO type), polyoxyethylene alkyl ethers, sucrose fatty acid esters, plant oils, and the like.

Specifically, caprylic acid, capric acid, caproic acid, lauric acid, myristic acid, palmitic acid, stearic acid, isostearic acid, oleic acid, linoleic acid, linolenic acid, lauryl alcohol, myristyl alcohol, oleyl alcohol, isostearyl alcohol, cetyl alcohol, lauric diethanolamide, myristyl myristate, octyldodecyl myristate, cetyl palmitate, methyl salicylate, ethylene glycol salicylate, cinnamic acid, methyl cinnamate, cresol, cetyl lactate, lauryl lactate, ethyl acetate, propyl acetate, geraniol, thymol, eugenol, terpineol, 1-menthol, borneol, d-limonene, isoeugenol, isoborneol, nerol, dl-camphor, glycerin monocaprylate, glycerin monocaprate, glycerin monolaurate, glycerin monooleate, sorbitan monolaurate, sucrose monolaurate, polysorbate 20, propylene glycol monolaurate, polyethylene glycol monolaurate, polyethylene glycol monostearate, polyoxyethylene oleyl ether, polyoxyethylene lauryl ether, HCO-60, pirotiodecane, and olive oil are preferable, among them, oleic acid, lauryl alcohol, myristyl alcohol, oleyl alcohol, isostearyl alcohol, lauric diethanolamide, 1-menthol, glycerin monocaprylate, glycerin monocaprate, glycerin monooleate, sorbitan monolaurate, propylene glycol monolaurate, polyoxyethylene oleyl ether, polyoxyethylene lauryl ether, and pirotiodecane are more preferable, and oleic acid, oleyl alcohol, and 1-menthol are preferably used. Since 1-menthol has analgesic effects and also has the effect of promoting the percutaneous absorption of the methyl salicylate, 1-menthol is contained in an amount of 1% by mass or more based on the total mass of the adhesive layer, and whereby topical anti-inflammatory analgesic effects can be improved.

The adhesive layer 3 in the adhesive patch 1 of the present invention may further contain a plasticizer. Examples of such a plasticizer include liquid paraffin, petroleum-based oils (such as paraffin-based process oil, naphthene-based process oil, and aromatic process oil), squalane, squalene, plant oils (such as olive oil, camellia oil, castor oil, tall oil, and peanut oil), silicone oil, dibasic acid ester (such as dibutyl phthalate and dioctyl phthalate), liquid rubbers (such as polybutene and liquid isoprene rubbers), glycol salicylate, and the like, and among them, liquid paraffin and liquid polybutene are preferably used.

Such plasticizers may be used in a mixture of two or more kinds, and the content of the plasticizer based on the whole composition constituting the adhesive layer 3 is appropriately determined within the range of 5 to 70% by mass, more preferably 10 to 60% by mass, and particularly preferably 10 to 50% by mass, based on the total mass of the adhesive layer, in consideration of maintaining sufficient permeability and sufficient cohesion as the adhesive patch.

Moreover, the adhesive layer 3 in the adhesive patch 1 of the present invention may further contain an antioxidant, a filler, a crosslinking agent, a preservative, a ultraviolet absorber, or the like, if necessary. Tocopherol and ester derivatives thereof, ascorbic acid, ascorbyl stearate, nordihydroguaiaretic acid, dibutylhydroxytoluene (BHT), butylated hydroxyanisole, and the like are desirable as such an antioxidant. Calcium carbonate, magnesium carbonate, silicate (e.g., aluminum silicate, magnesium silicate and the like), silicic acid, barium sulfate, calcium sulfate, calcium zincate, zinc oxide, titanium oxide, and the like are desirable as the filler. Amino resins, phenol resins, epoxy resins, alkyd resins, thermosetting resins such as unsaturated polyester and the like, isocyanate compounds, block isocyanate compounds, organic crosslinking agents, and inorganic crosslinking agents such as metals or metal compounds are desirable as the crosslinking agent. Ethyl parahydroxybenzoate, propyl parahydroxybenzoate, butyl parahydroxybenzoate, and the like are desirable as the preservative. p-aminobenzoic acid derivatives, anthranilic acid derivatives, salicylic acid derivatives, coumarin derivatives, amino acid-based compounds, imidazoline derivatives, pyrimidine derivatives, dioxane derivatives, and the like are desirable as the ultraviolet absorber.

Such an antioxidant, a filler, a crosslinking agent, a preservative, and a ultraviolet absorber are appropriately contained in an amount within the range of preferably 0.01 to 10% by mass, more preferably 0.1 to 5% by mass, and further preferably 0.2 to 2% by mass, based on the total mass of the adhesive patch.

Moreover, the adhesive patch 1 of the present invention may further comprise, in addition to the support 2 and the adhesive layer 3, a layer of a release coating that is peeled off in use, such as release sheet 4. Such an adhesive patch 1 is easily produced, stored and used and is therefore preferable. Examples of the release coating used in the present invention include release paper, cellophane, or synthetic resin films such as polyethylene, polypropylene, polyester, polyvinyl chloride and polyvinylidene chloride, subjected to release treatment (e.g., silicone treatment).

Next, a method for producing the adhesive patch 1 of the present invention will be described.

The production method of the adhesive patch 1 of the present invention is not particularly limited, and it can be produced by a so-called solvent or hot melt method. In the solvent method, each of constituents of the adhesive including the drug is first added to an organic solvent such as hexane, toluene or ethyl acetate so as to be respective predetermined proportions, and the mixture is stirred to obtain a uniform dissolved matter. Next, this dissolved matter is expanded onto the support 2, then dried with a drier to remove the organic solvent by volatilization and thereafter covered with a release coating, or alternatively, the dissolved matter may be expanded onto a release coating, then dried with a drier to remove the organic solvent by volatilization and thereafter transferred to the support 2 by compression.

In the hot melt method, the ingredients constituting the adhesive described above, except for the drug, are first heat-mixed in respective predetermined proportions under temperature conditions of 150° to 200° C. under an inert atmosphere such as nitrogen, then the drug is added thereto, and the mixture is further stirred to obtain a uniform melt. This melt is directly expanded onto the support 2 and covered with a release coating, and the resulting product is cut into a desired shape, or alternatively, this melt may be temporarily expanded onto a release coating and further cover the support 2 to transfer onto the support 2 by compression, and the resulting product may be thereafter cut into a desired shape. The hot melt method is preferably used in terms of good energy efficiency and being preferable for workers' health and environment.

The thickness (exclusive of the thicknesses of the support 2 and the release coating) of the adhesive layer 3 in the adhesive patch 1 is preferably 50 to 300 µm, more preferably 80 to 200 µm. Incidentally, when the thickness is less than 50 µm, the duration of adhesion or adhesiveness tends to be reduced, and on the other hand, when the thickness exceeds 300 µm, the cohesion and shape retention tend to be reduced.

Moreover, it is preferred that the adhesive layer 3 is formed such that the application amount (amount of inunction) of the adhesive layer 3 is 80 to 210 g/m² on the support 2. The application amount is more preferably 100 to 200 g/m², and further more preferably 120 to 180 g/m².

Incidentally, the order in which each base ingredient, the drug, and other additive ingredients are added in the production method described above is merely an example, and the method for producing the adhesive patch 1 is not limited to the method with this order of addition.

Next, the storage elastic modulus (G') of the adhesive layer 3 in the present invention will be described.

The useful adhesive layer 3 has the storage elastic modulus (G') at 10 rad/s (37° C.) preferably in the range of 30000 to 75000 Pa, more preferably in the range of 32000 to 70000 Pa and further more preferably in the range of 35000 to 65000 Pa. In this range, the adhesive patch having good application properties which suppresses seeping into the support 2 can be made. When the storage elastic modulus is less than 30000 Pa, application properties are not proper, such as the residual of plaster, and when exceeding 75000 Pa, drug release properties and percutaneous absorbability decrease, and the continuity of stimulation cannot be maintained.

Next, the moisture vapor permeability of the adhesive patch 1 of the present invention will be described.

It is preferred that the moisture vapor permeability is 1 to 350 g/m²·24 hr, when measured under conditions at a temperature of 40° C. and a relative humidity of 90% according to the method specified by JIS Z 208. From the viewpoint of being capable of further exerting good percutaneous absorbability and continuous application properties, the moisture vapor permeability is more preferably 1 to 200 g/m²·24 h, and further more preferably 1 to 100 g/m²·24 h.

Incidentally, the moisture vapor permeability of the adhesive patch 1 of the present invention depends on the thickness of the plaster and the degree of compression in the production of the adhesive patch, and a person skilled in the art can appropriately control the moisture vapor permeability to fall within the range described above.

Furthermore, the plasma $AUC_{0-24}$ (area under the blood concentration-time curve) and the plasma $C_{max}$ (maximum blood concentration) of methyl salicylate and its metabolite salicylic acid which is a substance that exhibits anti-inflammatory analgesic effects and 1-menthol in a case where 1% by mass or more based on the total mass of the adhesive layer in the adhesive patch 1 of the present invention will be described. Incidentally, in this context, the plasma concentrations of the drug and the metabolite are measured according to, for example, a guideline of FDA (U.S. Food and Drug Administration) (Gaidance for Industry=Bioanalytical Method Validation).

In the adhesive patch 1 of the present invention containing 10% or more of methyl salicylate based on the total mass of the adhesive layer, when the adhesive patch 1 is percutaneously administered in an amount of inunction of 50 to 300 g/m² to a 280 cm² area of a human for 8 hours, it is possible to ensure that the plasma $AUC_{0-24}$ of the methyl salicylate is 6 to 60 ng·hr/mL, the plasma $AUC_{0-24}$ of the salicylic acid is 2900 to 24000 ng·hr/mL, and the plasma $AUC_{0-24}$ of the 1-menthol is 13 to 220 ng·hr/mL, and thus topical anti-inflammatory analgesic effects can be sufficiently improved. Under the application conditions described above, it is preferred that the $AUC_{0-24}$ of the methyl salicylate, salicylic acid and 1-menthol are respectively 8 to 30 ng·hr/mL, 4000 to 8000 ng·hr/mL and 25 to 80 ng·hr/mL.

In addition, the adhesive patch 1 of the present invention, under the application conditions described above, it is possible to ensure that the plasma $C_{max}$ of the methyl salicylate is 2 to 125 ng/mL, the plasma $C_{max}$ of the salicylic acid is 450 to 2700 ng/mL, and the plasma $C_{max}$ of the 1-menthol is 2 to 30 ng/mL, and thus topical anti-inflammatory analgesic effects can be sufficiently improved. In this case, it is preferred that the $C_{max}$ of the methyl salicylate, salicylic acid and 1-menthol are respectively 5 to 20 ng/mL, 750 to 1400 ng/mL and 5 to 15 ng/mL.

According to the adhesive patch 1 of the present invention, the $AUC_{0-24}$ and $C_{max}$ within the ranges described above can be obtained. The $AUC_{0-24}$ and $C_{max}$ depend on the area of the adhesive patch 1, the thickness of the plaster, and an individual difference between human test subjects, and a person skilled in the art can appropriately control the parameters to fall within the predetermined numerical ranges by use of the adhesive patch 1 of the present invention. Alternatively, when the adhesive patch 1 of the present invention is applied to 70 cm² or other areas for 8 hours, it is obvious that the $AUC_{0-24}$ and $C_{max}$ get smaller according to reduction of the administration area. Moreover, the parameters described above are values obtained by use of the adhesive patch 1.

EXAMPLES

Hereinafter, while the present invention will be described more specifically on the basis of Examples and Comparative Examples, the present invention is not limited to the following Examples.

The ingredients constituting the adhesive layer (except for the drug) of the ingredients (% by mass) shown in Table 1, are heat-mixed in respective predetermined proportions at a temperature of 150 to 200° C. under an inert atmosphere such as nitrogen, then, the drug is added thereto, and the mixture is further stirred to obtain a uniform melt. Next, this melt was expanded onto a release coating and further cover polyethylene terephthalate (refer to Table 2) with stockinette stitch on both sides as a support to transfer onto the support 2 by compression, and the resulting product was thereafter cut into a square of 7×10 cm to produce an adhesive patch.

TABLE 1

| Name of Ingredient | Comparative Example 1 | Example 1 | Example 2 | Example 3 | Comparative Example 2 |
|---|---|---|---|---|---|
| Methyl Salicylate | 10 | 10 | 10 | 10 | 10 |
| l-Menthol | 3 | 3 | 3 | 3 | 3 |
| Styrene-isoprene-styrene Block Copolymer | 22 | 25 | 30 | 35 | 38 |
| Polyisobutylene | 5 | 10 | 5 | 5 | 5 |
| Liquid Paraffin | 40 | 35 | 32 | 27 | 24 |
| Alicyclic Saturated Hydrocarbon Resin | 20 | 17 | 20 | 20 | 20 |
| Total | 100 | 100 | 100 | 100 | 100 |

TABLE 2

| Material of Support | Type of Knitting | Modulus [N/5 cm] | Basis Weight [g/m$^2$] |
|---|---|---|---|
| Polyethylene Terephthalate | Stockinette Stitch on Both Sides | Longitudinal: 10 Lateral: 5 | 100 |

(Measurement of Storage Elastic Modulus)

Figure 3:
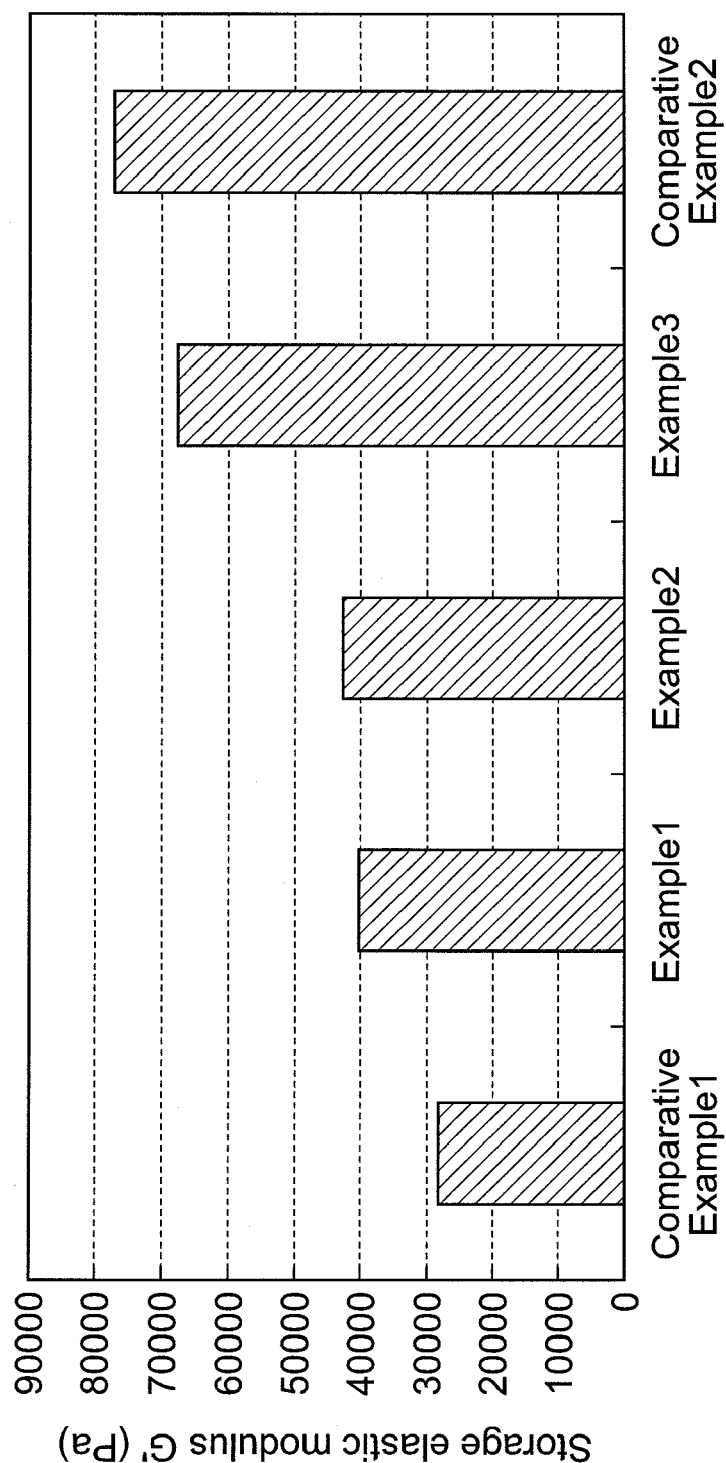
FIG. 3 is a graph showing the storage elasticity modulus (G') of each adhesive patch.

In order to obtain the storage elastic modulus (G') at each temperature and frequency, a dynamic viscoelastic measurement instrument (ARES: Advanced Rheometric Expansion System) was used. This apparatus was controlled with Orchestrator software version 6.5.8. Parallel plates of 8 mm diameter separated with a gap of about 2 mm were used. The number of measurement points is 10 points in each order, the sample was left for 3 seconds at each point, and the measurement temperature was defined at 37° C. The frequency was kept constant at 10 rad/s, the strain of the test was measured at 0.1 to 30%. After setting the measurement conditions described above, the strain-dependent measurement was started. The storage elastic modulus (G') was calculated from this strain data with a software. The results are shown in Table 3 and FIG. 3.

TABLE 3

| | Comparative Example 1 | Example 1 | Example 2 | Example 3 | Comparative Example 2 |
|---|---|---|---|---|---|
| Storage Elastic Modulus G' [Pa] | 28000 | 40000 | 43000 | 68000 | 77000 |

(Human Stimulation Test)

For Examples 1 to 3 and Comparative Examples 1 and 2, the sensory test was carried out according to the following method. The sample was applied to the right and left elbows of the arms or knees of the legs of six human subjects (healthy males) for 6 hours, and the continuity of stimulation and the residual of plaster after peeling off were evaluated. For the continuity of stimulation, the intensity of stimulation was evaluated by "appropriate" or "weak," and the residual of plaster was evaluated by the presence or absence of the plaster. The results are shown in Tables 4 and 5.

TABLE 4

| Continuity of Stimulation | Appropriate | Weak |
|---|---|---|
| Comparative Example 1 | 33% | 67% |
| Example 1 | 83% | 17% |
| Example 2 | 100% | 0% |
| Example 3 | 83% | 17% |
| Comparative Example 2 | 17% | 83% |

TABLE 5

| Residual of Plaster | Present | Absent |
|---|---|---|
| Comparative Example 1 | 67% | 33% |
| Example 1 | 0% | 100% |
| Example 2 | 0% | 100% |
| Example 3 | 0% | 100% |
| Comparative Example 2 | 0% | 100% |

Comparative Examples 1 and 2 are both weak in the continuity of stimulation, and the residual of plaster tends to be generated in Comparative Example 1. On the other hand, by Examples 1 to 3 having the storage elastic modulus (G') of 30000 to 75000 Pa, the adhesive patches excellent in the continuity of stimulation and application properties can be obtained. Incidentally, Examples 1 to 3 were good in application properties for 6 hours and did not cause irritation.

(Measurement of Moisture Vapor Permeability)

The moisture vapor permeability of the adhesive patch of Example 1 was measured at a temperature of 40° C. and a relative humidity of 90% according to the cup method (JIS Z0208).

As test pieces (n=3), those obtained by stamping the adhesive patch produced according to Example 1 into a round shape of approximately 70 mm in diameter were used, as a moisture absorbent, anhydrous calcium chloride (which has a particle size that passes through a 2380 μm standard sieve but remains on a 590 μm standard sieve) was used, as a cup, Y.S.S Tester No. 3525 (Yasuda Kikai Seisakusho, Ltd.) was used.

First, a glass dish containing the moisture absorbent was placed in the cup, and this cup was placed on a cup table kept in a horizontal position. The test piece was placed over the cup at a position concentric with the cup, with the support in the adhesive patch turned up, and a guide was put on the cup such that the guide fitted in a groove of the cup table. A ring was forced thereinto along with the guide until the test piece came into tight contact with the upper edge of the cup, and a weight was placed thereon, thereafter, the guide was removed by vertically pulling it up with care so as not to move the ring. Next, a molten sealing wax was poured into the groove on the periphery of the cup while the cup was horizontally rotated, to seal the edge of the test piece, and after the sealing wax was solidified, the weight and the cup table were removed to obtain test samples (n=3).

The initial mass of the cup was measured, and the test sample was thereafter left in a thermo-hygrostat kept under test conditions at a temperature of 40° C. and a relative humidity of 90% and taken out after 24 hours. The procedure of storing the test sample in a desiccator for 30 minutes and weighing the sample was repeated twice to measure the mass of the cup. A value obtained by subtracting the initial mass from this mass was defined as an amount of increase in mass, and the amount of increase in mass converted to a value per 1 m$^2$ was defined as moisture vapor permeability (g/m$^2$·24 h).

As a result, the moisture vapor permeability of the adhesive patch of Example 1 was 5 to 120 g/m$^2$·24 h.

(Measurement of Plasma Concentration)

The 280 cm$^2$ adhesive patch (methyl salicylate: 336 mg; 1-menthol: 100 mg) of Example 1 was applied to seven human subjects (healthy males) for 8 hours, and blood was collected over time. The blood was collected at each of 0, 0.5, 1, 2, 3, 4, 6, 8, 10, 12, 18, and 24 hours from the start of the application, and the amount of blood collected each time was 7 mL.

The plasma concentrations of the methyl salicylate, its metabolite salicylic acid, and the 1-menthol were each measured. The measurement was performed by liquid chromatography-mass spectrometry for the salicylic acid and by gas chromatography-mass spectrometry for the methyl salicylate and the 1-menthol. Each of the measurement methods was validated beforehand to confirm measurement reliability. Incidentally, values obtained by subtracting an endogenous concentration before the application (measurement value on 0 hour from the start of the application) from an actual measurement value were used as plasma concentrations during the application. The $C_{max}$ and $AUC_{0-24}$ were calculated according to the changes in the measurement values of these plasma concentrations over time.

Figure 4:
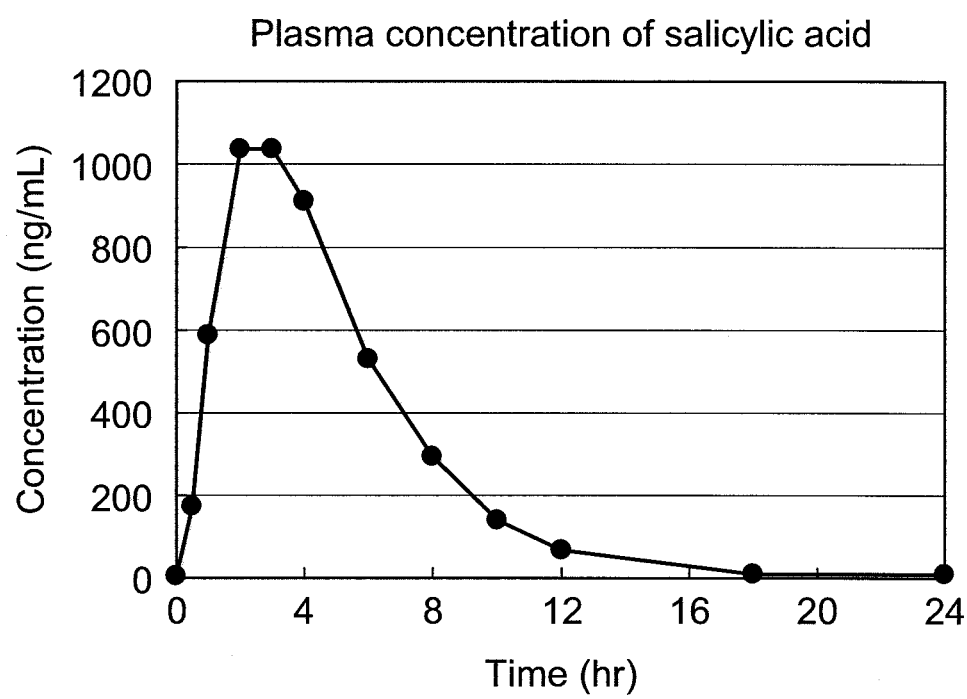
FIG. 4 is a graph showing changes in the plasma concentration of salicylic acid over time.
Figure 5:
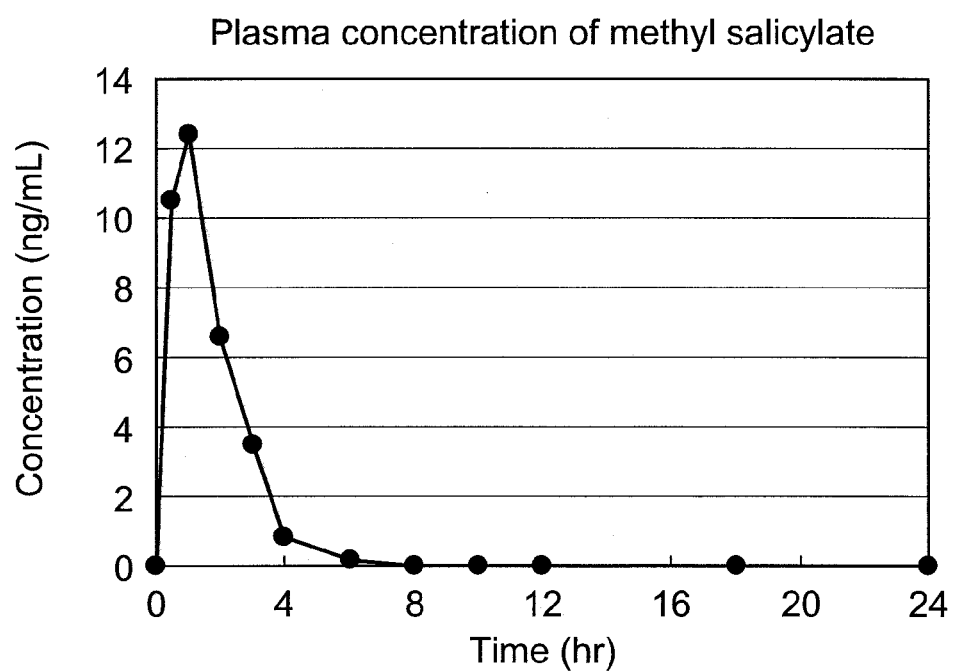
FIG. 5 is a graph showing changes in the plasma concentration of methyl salicylate over time.
Figure 6:
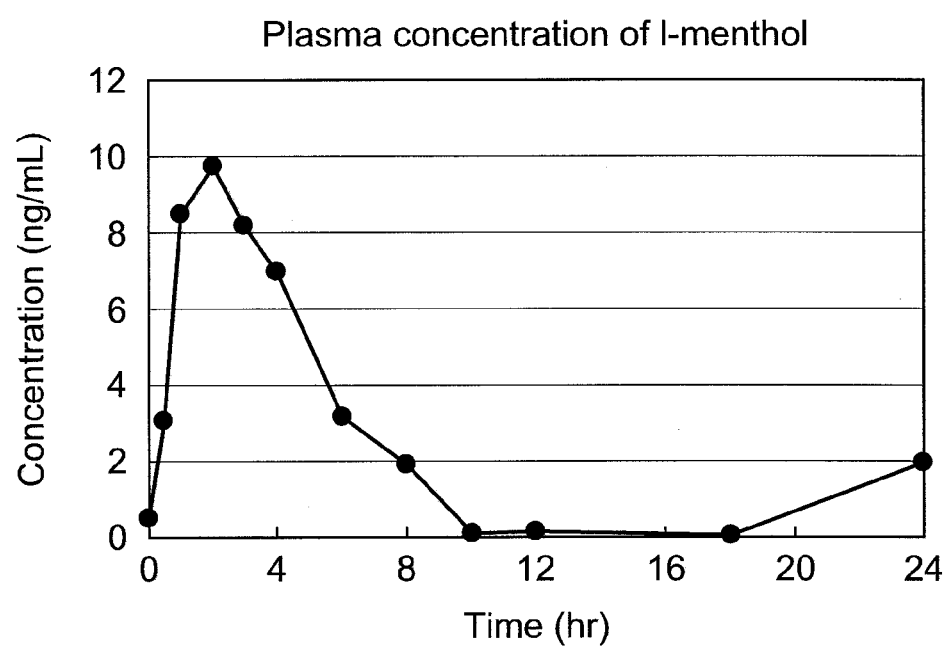
FIG. 6 is a graph showing changes in the plasma concentration of 1-menthol over time.

Changes in the plasma concentrations of the salicylic acid, the methyl salicylate, and the 1-menthol over time are shown in FIG. 4 to FIG. 6. In addition, the pharmacokinetic parameters (mean, maximum value, and minimum value of $C_{max}$ and $AUC_{0-24}$) of each of the drugs are shown in Table 6. Incidentally, a mean in the figure was an average value from the seven human subjects and represented using a standard deviation (SD). This measurement of the plasma concentrations was performed according to the guideline of FDA (U.S. Food and Drug Administration) (Gaidance for Industry=Bioanalytical Method Validation).

TABLE 6

|  |  | $AUC_{0-24}$ (ng · hr/mL) | Cmax (ng/mL) |
|---|---|---|---|
| Salicylic Acid | Mean ± SD | 6255 ± 2706 | 1078 ± 409 |
|  | Minimum Value | 3948 | 705 |
|  | Maximum Value | 11769 | 1771 |
| Methyl Salicylate | Mean ± SD | 24.9 ± 14.3 | 14.6 ± 10.9 |
|  | Minimum Value | 8.1 | 3.5 |
|  | Maximum Value | 50.0 | 33.0 |
| l-Menthol | Mean ± SD | 53.6 ± 33.4 | 10.7 ± 6.4 |
|  | Minimum Value | 15.4 | 4.5 |
|  | Maximum Value | 109 | 22.5 |

When each of the plasma parameters thus obtained is compared with a value obtained by subtracting a value on 0 hour from the plasma concentration of methyl salicylate or 1-menthol measured in Journal of Clin Pharmacol 2004; 44: 1151-1157, the $C_{max}$ and $AUC_{0-24}$ of the methyl salicylate and the 1-menthol in the applied 280 cm² of the adhesive patch (methyl salicylate: 336 mg; 1-menthol: 100 mg) of the present invention were close to the values of eight adhesive patches (methyl salicylate: 74.88 mg×8=599 mg; 1-menthol: 37.44× 8=299.5 mg) applied in Journal of Clin Pharmacol 2004; 44: 1151-1157. This demonstrated that, according to the adhesive patch of the present invention, the sufficient plasma concentration of each active ingredient is obtained. It is considered that the topical percutaneous absorption of the active ingredient is also sufficient by the adhesive patch of the present invention, and thus, it is considered that the adhesive patch of the present invention improves topical anti-inflammatory analgesic effects.

The invention claimed is:

1. An adhesive patch comprising a stretchable support and an adhesive layer laminated on at least one side of the support, wherein
   the stretchable support comprises a woven fabric knitted in stockinette stitch on both sides having two or more rows of crimped polyethylene terephthalate multifilament yarns,
   the adhesive layer comprising 37 to 45% by mass of a liquid organic ingredient and a plasticizer and 35 to 40% by mass of a thermoplastic elastomer based on the total mass of the layer and comprising 10% by mass or more of methyl salicylate as a liquid organic ingredient based on the total mass of the layer, and
   a storage elastic modulus (G') of the adhesive layer is 30000 to 75000 Pa at 10 rad/s and 37° C.

2. The adhesive patch according to claim 1, wherein the thermoplastic elastomer is at least one selected from the group consisting of a styrene-isoprene-styrene block copolymer, a styrene-butadiene-styrene block copolymer, a styrene-isoprene rubber, a styrene-butadiene rubber, polyisoprene, polybutadiene, polyisobutylene and a silicone rubber.

3. The adhesive patch according to claim 1, wherein the adhesive layer further comprises a rosin-based resin and/or a petroleum-based resin as a tackifier.

4. The adhesive patch according to claim 3, wherein a content of the tackifier is 10 to 30% by mass based on the total mass of the adhesive layer.

5. The adhesive patch according to claim 1, wherein the woven fabric has a basis weight of 80 to 150 g/m² and has a longitudinal (long axis direction) modulus of 2 to 12 N/5 cm and a lateral (short axis direction) modulus of 2 to 8 N/5 cm.

6. The adhesive patch according to claim 1, wherein a moisture vapor permeability of the entire adhesive patch measured at a temperature of 40° C. and a relative humidity of 90% is 1 to 350 g/m²·24 hr.

* * * * *

UNITED STATES PATENT AND TRADEMARK OFFICE
CERTIFICATE OF CORRECTION

PATENT NO.      : 8,382,729 B2  
APPLICATION NO. : 12/864183  
DATED           : February 26, 2013  
INVENTOR(S)     : Okada et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 261 days.

Signed and Sealed this
First Day of September, 2015

Michelle K. Lee
*Director of the United States Patent and Trademark Office*